(12) United States Patent
Nandi et al.

(10) Patent No.: US 11,318,145 B2
(45) Date of Patent: May 3, 2022

(54) ESLICARBAZEPINE SUSPENSION

(71) Applicant: Jubilant Generics Limited, Noida (IN)

(72) Inventors: Indranil Nandi, Yardley, PA (US); Tusharmouli Mukherjee, Yardley, PA (US); Dinesh Kumar, Noida (IN); Rakesh K. Singh, Noida (IN); Saurabh Srivastava, Noida (IN)

(73) Assignee: Jubilant Generics Limited

( * ) Notice: Subject to any disclaimer, the term of this patent is extended or adjusted under 35 U.S.C. 154(b) by 0 days.

(21) Appl. No.: 17/327,203

(22) Filed: May 21, 2021

(65) Prior Publication Data

US 2021/0275539 A1    Sep. 9, 2021

Related U.S. Application Data

(63) Continuation-in-part of application No. 16/827,534, filed on Mar. 23, 2020, which is a continuation-in-part of application No. PCT/IB2018/057400, filed on Sep. 25, 2018.

(51) Int. Cl.

| | |
|---|---|
| A61K 31/55 | (2006.01) |
| A61K 47/26 | (2006.01) |
| A61K 47/14 | (2017.01) |
| A61K 47/38 | (2006.01) |
| A61K 9/00 | (2006.01) |
| A61K 9/10 | (2006.01) |
| A61K 47/22 | (2006.01) |
| A61K 47/10 | (2017.01) |
| A61K 47/42 | (2017.01) |
| A61K 47/36 | (2006.01) |
| A61K 47/02 | (2006.01) |
| A61K 47/12 | (2006.01) |

(52) U.S. Cl.
CPC ............ *A61K 31/55* (2013.01); *A61K 9/0053* (2013.01); *A61K 9/10* (2013.01); *A61K 47/02* (2013.01); *A61K 47/10* (2013.01); *A61K 47/12* (2013.01); *A61K 47/14* (2013.01); *A61K 47/22* (2013.01); *A61K 47/26* (2013.01); *A61K 47/36* (2013.01); *A61K 47/38* (2013.01); *A61K 47/42* (2013.01)

(58) Field of Classification Search
CPC ........ A61K 31/55; A61K 9/0053; A61K 9/10; A61K 47/02; A61K 47/10; A61K 47/12; A61K 47/14; A61K 47/22; A61K 47/26; A61K 47/36; A61K 47/38; A61K 47/42
See application file for complete search history.

(56) References Cited

U.S. PATENT DOCUMENTS

| | | | |
|---|---|---|---|
| 2009/0291981 A1* | 11/2009 | Schaab | A61P 9/00 546/256 |
| 2013/0040939 A1 | 2/2013 | de Vasconcelos | |
| 2014/0294972 A1* | 10/2014 | White | A61K 9/0095 424/489 |

FOREIGN PATENT DOCUMENTS

| WO | 2009054743 A1 | | 4/2009 |
|---|---|---|---|
| WO | WO 2011/031176 | * | 3/2011 |
| WO | 2017103876 A1 | | 6/2017 |

* cited by examiner

*Primary Examiner* — Genevieve S Alley
(74) *Attorney, Agent, or Firm* — William D. Hare, Esq.; McNeely, Hare & War, LLP

(57) ABSTRACT

The present invention relates to oral ready to use liquid pharmaceutical compositions of eslicarbazepine. It also relates to the processes for the preparation of said liquid compositions. The present invention provides liquid compositions of eslicarbazepine with desired technical attributes such as release profile, viscosity, pH, stability, and acceptable organoleptic properties. The prepared compositions are useful in patients having difficulties in swallowing tablets and provide the physician with providing a more convenient and less cumbersome posology.

20 Claims, 1 Drawing Sheet

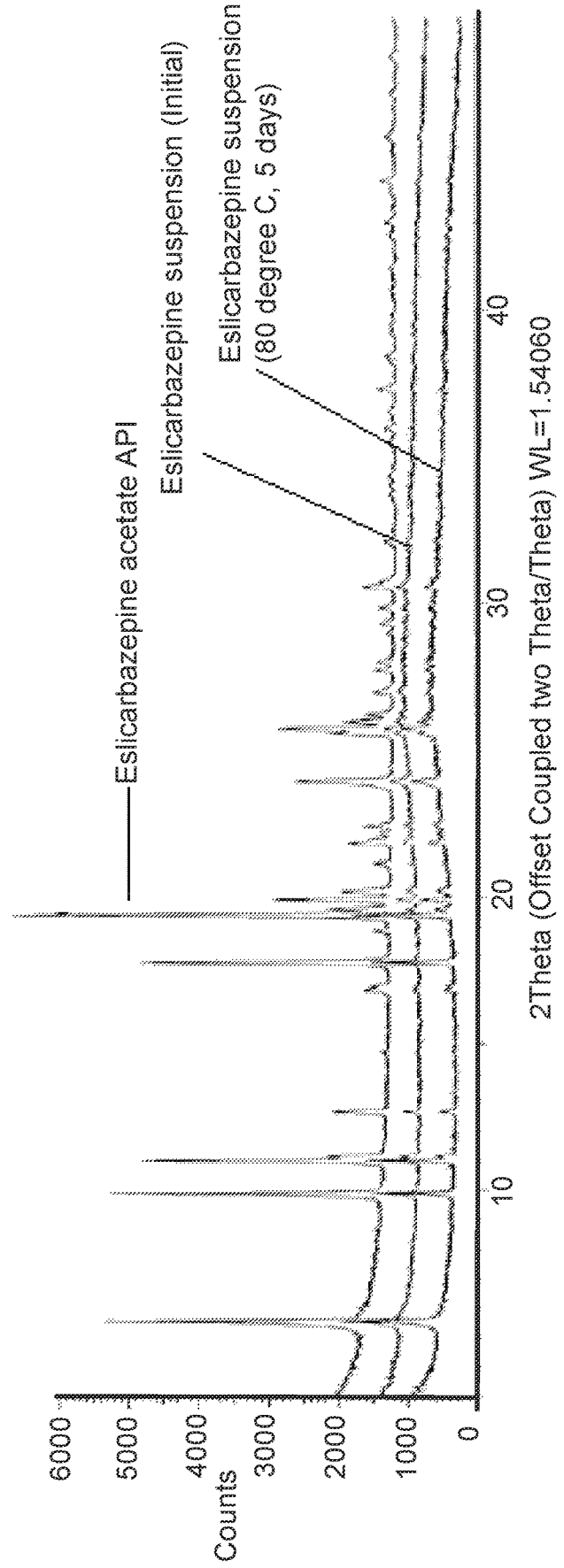

ESLICARBAZEPINE SUSPENSION

FIELD OF THE INVENTION

The present invention relates to orally administered liquid pharmaceutical compositions of eslicarbazepine. The liquid compositions are in the form of ready to use suspension and suspension powder for reconstitution. It also relates to the processes for the preparation of said liquid compositions.

BACKGROUND OF THE INVENTION

Eslicarbazepine acetate is an anticonvulsant drug. It is chemically known as (S)-10-acetoxy-10,11-dihydro-5H-dibenz [b,f]azepine-5-carboxamide.

Eslicarbazepine acetate is marketed in the United States as an immediate release tablet in 200 mg, 400 mg, 600 mg and 800 mg strengths under the brand name APTIOM® (Eslicarbazepine acetate Oral Tablets 200 mg, 400 mg, 600 mg and 800 mg) by Sunovion Pharmaceuticals. The marketed solid dosage form of eslicarbazepine is indicated for the treatment of partial onset seizures.

The tablet dosage form of eslicarbazepine has a large tablet size and weight. Difficulty in swallowing large tablets and capsules (dysphagia) is a problem for many patients and can lead to a variety of adverse events as well as induce significant non-compliance with the prescribed treatment regimens. Adolescents, children, and the elderly are particularly vulnerable population groups that are more likely than adults to experience difficulty in swallowing large tablets or capsules. Liquid dosage forms are designed with an objective of minimizing swallowing difficulties and are likely to improve patient compliance by reducing dysphagia-related adverse events due to large tablet size and accordingly providing a more convenient and less cumbersome posology U.S. Publication No. 2013/0040939 discloses oral suspension formulations of eslicarbazepine acetate comprising xanthan gum as a suspending agent, polyoxyethylene stearate as a wetting agent, and saccharin sodium as a sweetener. Xanthan gum suffers from drawbacks such as microbial contamination and causes side effects such as allergic reactions, flatulence, bloating and stomach upset. Sodium saccharin is not preferred as a sweetener as it has carcinogenic potential.

There exists an unmet need in the art to provide liquid compositions of eslicarbazepine acetate which are stable, provide ease of administration, dose adjustment, and enhanced patient compliance. The inventors of the present invention have prepared eslicarbazepine ready to use suspension and suspension powder for reconstitution convenient for administration by pediatric and geriatric patients, easy to manufacture, palatable, functionally reproducible, and provide ease of dose adjustment. Further, the liquid compositions exhibit desirable technical attributes.

OBJECTS AND SUMMARY OF THE INVENTION

It is a principal object of the present invention to provide a stable immediate release oral liquid pharmaceutical composition comprising an anticonvulsant drug with one or more pharmaceutically acceptable excipients and processes for its preparation.

It is another object of the present invention to provide a pharmaceutical suspension comprising eslicarbazepine or its pharmaceutically acceptable esters, salts, solvates, polymorphs, enantiomers or mixtures thereof with one or more pharmaceutically acceptable excipients and/or carrier and process for their preparation.

It is another object of the present invention to provide a suspension powder for reconstitution comprising eslicarbazepine or its pharmaceutically acceptable esters, salts, solvates, polymorphs, enantiomers or mixtures thereof with one or more pharmaceutically acceptable excipients and/or carrier and process for their preparation.

It is another object of the present invention to provide an oral liquid pharmaceutical composition in the form of a suspension comprising eslicarbazepine or its pharmaceutically acceptable esters, salts, solvates, polymorphs, enantiomers or mixtures thereof with one or more pharmaceutically acceptable excipients and/or carrier wherein the pharmaceutically acceptable excipients are selected from the group comprising of suspending agent, antioxidant, anticaking agent, antifoaming agent, pH adjusting agent, coloring agent, sweetening agent, flavoring agent, surfactant/solubilizer/wetting agent, buffer, diluent, preservative and mixtures thereof. The suspension is in the form of ready to use suspension and suspension powder for reconstitution.

The following embodiments further describe the objects of the present invention in accordance with the best mode of practice, however, the disclosed invention is not restricted to the particular embodiments hereinafter described.

In accordance with one embodiment of the present invention, there is provided an immediate release oral pharmaceutical suspension dosage form comprising:

a) eslicarbazepine or its pharmaceutically acceptable salts, esters, hydrates or polymorphs thereof present at from about 0.1% to about 40% w/w;

b) suspending agent present at from about 0.01% to about 10% w/w; and c) surfactant present at from 0% to about 7% w/w; wherein the dosage form is free from xanthan gum and/or polyoxyethylene stearate.

In accordance with another embodiment of the present invention, there is provided an immediate release oral pharmaceutical suspension dosage form comprising:

a) eslicarbazepine or its pharmaceutically acceptable salts, esters, hydrates or polymorphs thereof present at from about 0.1% to about 40% w/w;

b) suspending agent present at from about 0.01% to about 10% w/w; and c) surfactant present at from 0% to about 7% w/w; wherein the pH of the suspension is from 3 to 8 and the dosage form is free from xanthan gum and/or polyoxyethylene stearate.

In accordance with another embodiment of the present invention, there is provided an immediate release oral pharmaceutical suspension dosage form comprising:

a) eslicarbazepine or its pharmaceutically acceptable salts, esters, hydrates or polymorphs thereof present at from about 0.1% to about 40% w/w;

b) suspending agent present at from about 0.01% to about 10% w/w; and c) surfactant present at from 0% to about 7% w/w; and d) pharmaceutically acceptable liquid carrier; wherein the dosage form is free from xanthan gum and/or polyoxyethylene stearate.

In accordance with another embodiment of the present invention, there is provided an immediate release oral pharmaceutical suspension dosage form comprising:

a) eslicarbazepine or its pharmaceutically acceptable salts, esters, hydrates or polymorphs thereof present at from about 0.1% to about 40% w/w;

b) suspending agent present at from about 0.01% to about 10% w/w; and c) surfactant present at from 0% to about 7% w/w;

wherein the dosage form is free from xanthan gum and/or polyoxyethylene stearate and exhibits more than 65% of drug release within 20 minutes, when placed in a dissolution vessel filled with 1000 ml of acetate buffer, pH 4.5 maintained at 37±0.5° C. and stirred at a paddle speed of 100 rpm using a USP Type II (paddle) apparatus.

In accordance with another embodiment of the present invention, the immediate release oral pharmaceutical suspension dosage form of eslicarbazepine is a ready to use suspension. In another embodiment, the immediate release oral pharmaceutical suspension dosage form of eslicarbazepine is a suspension powder for reconstitution.

In accordance with another embodiment of the present invention, the immediate release oral pharmaceutical suspension dosage form has eslicarbazepine in an amount from about 0.1 mg/mL to about 200 mg/mL and a viscosity of from about 700 cps to about 1200 cps.

In accordance with another embodiment of the present invention, there is provided an immediate release oral pharmaceutical suspension dosage form of eslicarbazepine or its pharmaceutically acceptable salts, esters, hydrates or polymorphs thereof with one or more pharmaceutically acceptable excipients comprising:

a) suspending agent;

b) preservative;

c) optionally a surfactant;

d) optionally an antioxidant;

e) pH adjusting agent to maintain the pH of the composition in the range of about 3 to about 8; and/or pharmaceutically acceptable liquid carrier; wherein the composition is free of xanthan gum and/or polyoxyethylene stearate.

In accordance with another embodiment of the present invention, there is provided an immediate release oral pharmaceutical suspension dosage form of eslicarbazepine or its pharmaceutically acceptable salts, esters, hydrates or polymorphs thereof with one or more pharmaceutically acceptable excipients comprising:

a) suspending agent;

b) diluent;

c) preservative;

d) optionally an antioxidant;

e) pH adjusting agent to maintain the pH of the composition in the range of about 3 to about 8; and/or pharmaceutically acceptable liquid carrier, wherein the suspending agent is selected from the group comprising gellan gum, cellulose and its derivatives, a mixture of carboxymethylcellulose and microcrystalline cellulose, propylene glycol alginate, and combinations thereof.

In accordance with another embodiment of the present invention, there is provided an immediate release oral pharmaceutical suspension dosage form of eslicarbazepine or its pharmaceutically acceptable salts, esters, hydrates or polymorphs thereof with one or more pharmaceutically acceptable excipients comprising:

a) a suspending agent;

b) a surfactant;

c) a preservative;

d) optionally an antioxidant;

e) pH adjusting agent in sufficient amounts to maintain the pH of the composition in the range of about 3 to about 8; and/or pharmaceutically acceptable liquid carrier, wherein the surfactant is selected from the group comprising non-ionic surfactants, anionic, cationic or zwitterionic surfactants with the proviso that the surfactant is not polyoxyethylene stearate.

In accordance with another embodiment of the present invention, there is provided an immediate release oral pharmaceutical suspension dosage form of eslicarbazepine or its pharmaceutically acceptable salts, esters, hydrates or polymorphs thereof with one or more pharmaceutically acceptable excipients comprising eslicarbazepine present at from about 0.1 mg/mL to about 200 mg/mL, wherein the pH of the composition is from 3 to 8.

In accordance with another embodiment of the present invention, there is provided an immediate release oral pharmaceutical suspension dosage form of eslicarbazepine or its pharmaceutically acceptable salts, esters, hydrates or polymorphs thereof with one or more pharmaceutically acceptable excipients comprising eslicarbazepine present at from about 0.1 mg/mL to about 200 mg/mL, wherein the pH of the composition is from 3 to 8 and the viscosity is from 700 cps to 1200 cps.

In accordance with a one embodiment of the present invention, there is provided a suspension powder for reconstitution comprising eslicarbazepine or its pharmaceutically acceptable esters, salts, hydrates or polymorphs thereof and at least one or more pharmaceutically acceptable excipients selected from the group comprising suspending agent/thickening agent/viscosity agent, antioxidant, anticaking agent, antifoaming agent, pH adjusting agent, coloring agent, sweetening agent, flavoring agent, surfactant/wetting agent, buffer, diluent and preservative.

In accordance with one embodiment of the present invention, there is provided a ready to use stable liquid suspension comprising eslicarbazepine or its pharmaceutically acceptable esters, salts, esters, hydrates or polymorphs thereof and at least one or more pharmaceutically acceptable excipients and/or carrier wherein the pharmaceutically acceptable excipient is selected from the group comprising a thickening agent/viscosity agent, antioxidant, anticaking agent, antifoaming agent, pH adjusting agent, coloring agent, sweetening agent, flavoring agent, surfactant/wetting agent, buffer, diluent, taste-masking agent, and preservative.

In accordance with another embodiment of the present invention, there is provided dry powder for suspension compositions suitable for use as a liquid suspension for children or elderly patients. The compositions include eslicarbazepine or its pharmaceutically acceptable salts, esters, hydrates or polymorphs thereof and pharmaceutically acceptable excipients selected from the group consisting of suspending agents, coating agents, preservatives, flavoring agents, sweeteners, lubricants, surfactants, buffering agents, and diluents.

In accordance with still another embodiment of the present invention, there is provided a process for the preparation of a stable pharmaceutical composition in the form of a suspension comprising eslicarbazepine or its pharmaceutically acceptable salts, esters, hydrates or polymorphs thereof.

In accordance with still another embodiment of the present invention, there is provided a process for the preparation of a stable pharmaceutical composition in the form of a suspension comprising eslicarbazepine or its pharmaceutically acceptable esters, salts, hydrates or polymorphs thereof in micronized form.

In accordance with still another embodiment of the present invention, there is provided a process for the preparation of a ready to use liquid suspension of eslicarbazepine or its pharmaceutically acceptable salts, esters, hydrates or polymorphs thereof, comprising combining various components using conventional equipment such as overhead stirrers, ultrasonifiers, mills, and homogenizers. Many different orders of adding components can be employed.

In accordance with still another embodiment of the present invention, there is provided a process for the preparation of a dry powder for suspension composition of eslicarbazepine or its pharmaceutically acceptable salts, esters, hydrates or polymorphs thereof, which is suitable for suspension in water and/or water miscible suitable solvents to form an orally administrable product which comprises admixing eslicarbazepine granules with substantially dry pharmaceutically acceptable excipients selected from the group consisting of suspending agents/viscosity enhancers, coating agents, preservatives, flavoring agents, sweeteners, lubricants, wetting agents, surfactants, buffering agents, and diluents to form a dry admixture, and transferring the dry admixture to a sealable storage container.

In accordance with still another embodiment of the present invention, there is provided a stable pharmaceutical composition in the form of a suspension comprising eslicarbazepine or its pharmaceutically acceptable salts, esters, hydrates or polymorphs thereof, wherein the composition is substantially free from other polymorphic forms.

In accordance with still another embodiment of the present invention, there is provided a stable pharmaceutical composition in the form of a suspension comprising eslicarbazepine or its pharmaceutically acceptable salts, esters, hydrates or polymorphs thereof, wherein eslicarbazepine has a particle size distribution $D_{90}$ less than about 200 µm.

In accordance with still another embodiment of the present invention, there is provided a stable pharmaceutical composition in the form of a suspension comprising eslicarbazepine or its pharmaceutically acceptable salts, esters, hydrates or polymorphs thereof, in an amount of about 0.01% to about 90% by weight, wherein the composition exhibits desirable technical attributes like pourability, viscosity, dissolution, stability, re-suspendability and re-dispersibility.

In accordance with still another embodiment of the present invention, there is provided a use of a stable pharmaceutical composition in the form of a suspension comprising eslicarbazepine or its pharmaceutically acceptable salts, hydrates or polymorphs, thereof, for the treatment of epilepsy, neuropathic pain, migraine, fibromyalgia, trigeminal neuralgia, bipolar disorders, attention disorders, anxiety disorders, affective disorders, schizoaffective disorders, sensorimotor disorders, and vestibular disorders.

In accordance with still another embodiment of the present invention, there is provided a kit comprising: (a) an immediate release oral pharmaceutical suspension dosage form comprising eslicarbazepine or its pharmaceutically acceptable salts, esters, hydrates or polymorphs thereof with one or more pharmaceutically acceptable excipients and/or carrier, (b) a dispensing and/or dosing syringe for administering the composition; and (c) optionally, instructions for preparation and use.

BRIEF DESCRIPTION OF THE FIGURE

FIG. 1 shows an overlay of the x-ray diffraction patterns of eslicarbazepine acetate drug substance and eslicarbazepine suspension (initial) and eslicarbazepine suspension stability samples (stored at 80° C. for 5 days) as per Example 11.

DETAILED DESCRIPTION OF THE INVENTION

The present invention can be more readily understood by the following detailed description of the invention and study of the included examples.

As used herein, the term "composition" or "formulation" or "dosage form", as in pharmaceutical composition, is intended to encompass a drug product comprising an anti-convulsant or anti-epileptic drug, preferably eslicarbazepine or its pharmaceutically acceptable salts, esters, solvates, polymorphs, enantiomers or mixtures thereof, and other inert ingredient(s) (pharmaceutically acceptable excipients). Such pharmaceutical compositions are synonymous with "formulation" and "dosage form". The pharmaceutical compositions of the present invention include, but are not limited to powder for suspension, ready to use suspension and the like.

As used herein, the term "ready to use suspension" means a pre-constituted suspension which can be administered as such. The "powder for suspension" or "dry suspension" needs to be reconstituted with a liquid carrier to form a suspension before administration.

As used herein, the term "eslicarbazepine" is used in a broad sense to include not only "eslicarbazepine" per se but also its pharmaceutically acceptable salts, solvates, hydrates, enantiomers, derivatives, isomers, polymorphs, metabolites, prodrugs thereof, and also its various crystalline and amorphous forms. In particular, the salt of eslicarbazepine is eslicarbazepine acetate. The term "eslicarbazepine acetate" used in this specification means the S-isomer in substantially pure form, i.e. at least about 98% pure.

The term "excipient" means a pharmacologically inactive component such as a suspending agent/viscosity agent, anticaking agent, antifoaming agent, pH adjusting agent, antioxidant, sweetening agent, flavoring agent, surfactant/solubilizer/wetting agent, buffer, and preservative and the like. The excipients used in preparing the liquid pharmaceutical composition are safe and non-toxic. Reference to an excipient includes both one and more than one such excipient. Co-processed excipients are also covered under the scope of the present invention. Combinations of excipients performing the same function may also be used to achieve desired formulation characteristics.

As used herein, the term "about" means±approximately 20% of the indicated value, such that "about 10 percent" indicates approximately 08 to 12 percent.

As used in this specification, the singular forms "a", "an", and "the" include plural references unless the context clearly dictates otherwise. Thus, for example, a reference to "a process" includes one or more process, and/or steps of the type described herein and/or which will become apparent to those persons skilled in the art upon reading this disclosure and so forth.

The term "stable," as used herein, refers to chemical stability, wherein not more than 5% w/w of total related substances are formed on storage at 40° C. and 75% relative humidity (R.H.) or at 25° C. and 60% R.H. for a period of at least one month, particularly for a period of two months, and more particularly for a period of at least three months.

The term "sedimentation volume ratio," or "sedimentation ratio," refers to a ratio of the ultimate volume of sediment (Vu) to the original volume of sediment ($V_O$) before settling. It also refers to a ratio of the ultimate height of sediment (Hu) to the initial of sediment ($H_O$) before settling. The term "taste-masking agents", when used herein, refers to taste receptor blockers, compounds that mask the chalkiness, grittiness, dryness, and/or astringent or bitter taste properties of an active compound.

Unless otherwise stated the weight percentages expressed herein are based on the final weight of the composition or formulation.

The present invention is a stable pharmaceutical composition directed to ready to use oral liquid suspension or dry powder for suspension compositions suitable for use as a liquid suspension for administration to a subject in need thereof which comprises eslicarbazepine or its pharmaceutically acceptable salts, esters, hydrates or polymorphs thereof.

In accordance with one embodiment of the present invention, there is provided a stable pharmaceutical composition in the form of a suspension comprising eslicarbazepine or its pharmaceutically acceptable salts, esters, hydrates or polymorphs thereof with one or more pharmaceutically acceptable excipient and/or liquid carrier and process for its preparation.

Another embodiment of the present invention relates to an immediate release oral pharmaceutical suspension dosage form of eslicarbazepine or its pharmaceutically acceptable salts, esters, hydrates or polymorphs thereof with one or more pharmaceutically acceptable excipients comprising:
  a) suspending agent;
  b) preservative;
  c) optionally a surfactant;
  d) optionally an antioxidant;
  e) pH adjusting agent to maintain the pH of the composition in the range of about 3 to about 8; and/or pharmaceutically acceptable liquid carrier.

In accordance with another embodiment of present invention, there is provided a suspension comprising eslicarbazepine or its pharmaceutically acceptable salts, esters, hydrates or polymorphs thereof and one or more pharmaceutically acceptable excipients and/or a liquid carrier, wherein the composition is free of xanthan gum.

In accordance with another embodiment of present invention, there is provided a suspension comprising eslicarbazepine or its pharmaceutically acceptable salts, esters, hydrates or polymorphs thereof and one or more pharmaceutically acceptable excipients and/or a liquid carrier, wherein the composition is free of polyoxyethylene stearate.

In accordance with another embodiment of present invention, there is provided a stable suspension comprising eslicarbazepine or its pharmaceutically acceptable salts, esters, hydrates or polymorphs thereof and one or more pharmaceutically acceptable excipients and/or a liquid carrier, wherein the composition is free of xanthan gum and polyoxyethylene stearate.

In accordance with another embodiment of the present invention, there is provided an immediate release oral ready to use suspension comprising:
  a) eslicarbazepine or its pharmaceutically acceptable salts, esters, hydrates or polymorphs thereof at from about 0.1% to about 40% w/w;
  b) suspending agent at from about 0.01% to about 10% w/w;
  c) surfactant at from about 0.01% to about 7% w/w; and
  d) pharmaceutically acceptable liquid carrier at from about 10% to about 95% w/w;
wherein the suspension is free from xanthan gum and polyoxyethylene stearate.

In accordance with another embodiment of the present invention, there is provided an immediate release oral ready to use suspension of comprising:
  a) eslicarbazepine or its pharmaceutically acceptable salts, esters, hydrates or polymorphs thereof at from about 0.1% to about 40% w/w;
  b) a suspending agent at from about 0.01% to about 10% w/w; and
  c) a surfactant from at about 0.01% to about 7% w/w; and
  d) a pharmaceutically acceptable liquid carrier at from about 10% to about 95% w/w;
wherein the ratio of eslicarbazepine:suspending agent ranges from 1:0.01 to 1:4 by weight and the suspension is free of xanthan gum and polyoxyethylene stearate.

In accordance with another embodiment of the present invention, there is provided an immediate release oral ready to use suspension, wherein the suspension comprises:
  a) eslicarbazepine or its pharmaceutically acceptable salts, esters, hydrates or polymorphs thereof at from about 0.1% to about 40% w/w;
  b) a suspending agent at from about 0.01% to about 10% w/w;
  c) a surfactant at from about 0.01% to about 7% w/w; and
  d) a pharmaceutically acceptable liquid carrier at from about 10% to about 95% w/w;
wherein the pH of the suspension is from 3 to 6.5 and the suspension is free of xanthan gum and polyoxyethylene stearate.

In accordance with another embodiment of the present invention, there is provided an immediate release oral ready to use suspension, wherein there is no change in the polymorphic form of eslicarbazepine for at least 5 days when the suspension is stored at 80° C.

In accordance with another embodiment of the present invention, there is provided an immediate release oral ready to use suspension, wherein the suspension is stable when stored at 40° C./75% R.H. for a period of at least 3 months.

In accordance with another embodiment of the present invention, there is provided an immediate release oral ready to use suspension, wherein the viscosity of the suspension is from 100 to 5000 cps.

In accordance with another embodiment of the present invention, there is provided an immediate release oral ready to use suspension, wherein the viscosity of the suspension is from 100 to 2500 cps.

In accordance with another embodiment of the present invention, there is provided an immediate release oral ready to use suspension, wherein the amount of eslicarbazepine is from about 0.1 mg/mL to about 400 mg/mL.

In accordance with another embodiment of the present invention, there is provided an immediate release oral ready to use suspension comprising:
  a) eslicarbazepine or its pharmaceutically acceptable salts, esters, hydrates or polymorphs thereof;
  b) suspending agent;
  c) surfactant;
  d) preservative;
  e) pH adjusting agent or buffering agent;
  f) sweetening agent; and
  h) pharmaceutically acceptable liquid carrier;
wherein the suspension is free from xanthan gum and polyoxyethylene stearate.

In accordance with another embodiment of the present invention, there is provided an immediate release oral ready to use suspension comprising:
  a) eslicarbazepine or its pharmaceutically acceptable salts, esters, hydrates or polymorphs thereof;
  b) co-processed spray dried forms of microcrystalline cellulose and carboxymethyl cellulose sodium as suspending agent;

c) surfactant;
d) preservative;
e) pH adjusting agent or buffering agent;
f) sweetening agent;
g) flavoring agent; and
h) pharmaceutically acceptable liquid carrier;

wherein the suspension is free from xanthan gum and polyoxyethylene stearate.

In accordance with another embodiment of the present invention, there is provided an immediate release oral ready to use suspension comprising:
a) eslicarbazepine or its pharmaceutically acceptable salts, esters, hydrates or polymorphs thereof;
b) one or more suspending agents selected from cellulose derivatives and co-processed spray dried forms of microcrystalline cellulose and carboxymethyl cellulose sodium, carbomers, gums, pectin, propylene glycol alginate, dextran; gelatin, polyethylene glycols, polyvinyl compounds, sugar alcohols, colloidal silica, maltodextrin, starch, or a combination thereof;
c) surfactant;
d) preservative;
e) pH adjusting agent or buffering agent;
f) sweetening agent;
g) flavoring agent; and
h) pharmaceutically acceptable liquid carrier;

wherein the suspension is free from xanthan gum and polyoxyethylene stearate.

In accordance with another embodiment of the present invention, there is provided an immediate release oral ready to use suspension comprising:
a) eslicarbazepine or its pharmaceutically acceptable salts, esters, hydrates or polymorphs thereof at from about 0.1% to about 40% w/w;
b) suspending agent at from about 0.01% to about 10% w/w;
c) surfactant at from about 0.01% to about 7% w/w;
d) preservative at from about 0.001% to about 4% w/w;
e) pH adjusting agent or buffering agent at from about 0.01% to about 15% w/w;
f) sweetening agent at from about 0.01% to about 70% w/w;
g) flavoring agent at from about 0.01% to about 5% w/w; and
h) pharmaceutically acceptable liquid carrier at from about 10% to about 95% w/w;

wherein the suspension is free from xanthan gum and polyoxyethylene stearate.

In accordance with another embodiment of the present invention, there is provided an immediate release oral ready to use suspension comprising:
a) eslicarbazepine or its pharmaceutically acceptable salts, esters, hydrates or polymorphs thereof;
b) co-processed spray dried forms of microcrystalline cellulose and carboxymethyl cellulose sodium or a combination thereof;
c) polyoxyethylene sorbitan fatty acid ester surfactant;
d) paraben;
e) citric acid and trisodium citrate buffer;
f) sorbitol or thaumatin or a combination thereof;
g) flavoring agent;
h) glycerin; and
i) water.

wherein the suspension is free from xanthan gum and polyoxyethylene stearate.

In accordance with another embodiment of the present invention, there is provided an immediate release oral ready to use suspension comprising:
a) eslicarbazepine or its pharmaceutically acceptable salts, esters, hydrates or polymorphs thereof at from about 0.1% to about 40% w/w;
b) co-processed spray dried forms of microcrystalline cellulose and carboxymethyl cellulose sodium, or a combination thereof at from about 0.01% to about 10% w/w;
c) polyoxyethylene sorbitan fatty acid ester surfactant at from about 0.01% to about 7% w/w;
d) paraben at from about 0.001% to about 3% w/w;
e) citric acid and trisodium citrate buffer at from about 0.005% to about 4% w/w;
f) sorbitol or thaumatin or a combination thereof at from about 0.01% to about 70% w/w;
g) flavoring agent at from about 0.01% to about 5% w/w; and
h) glycerin, and
i) water, wherein the suspension is free from xanthan gum and polyoxyethylene stearate.

In accordance with another aspect of the present embodiment, there is provided an immediate release oral pharmaceutical ready to use suspension comprising:
(a) eslicarbazepine or its pharmaceutically acceptable salts, esters, hydrates or polymorphs thereof at from about 0.1% to about 40% w/w;
(b) suspending agent at from about 0.01% to about 10% w/w; and
(c) surfactant at from about 0.01% to about 7% w/w; and
(d) pharmaceutically acceptable liquid carrier at from about 10% to about 95% w/w;

wherein the suspension is free of xanthan gum and polyoxyethylene stearate and exhibits more than 75% of drug release within 15 minutes, when placed in a dissolution vessel filled with 1000 ml of acetate buffer, pH 4.5 maintained at 37±0.5° C. and stirred at a paddle speed of 100 rpm using a USP Type II (paddle) apparatus.

In accordance with another embodiment of the present invention, there is provided an immediate release oral ready to use suspension comprising:
a) eslicarbazepine or its pharmaceutically acceptable salts, esters, hydrates or polymorphs thereof at from about 0.1% to about 40% w/w;
b) a suspending agent at from about 0.01% to about 10% w/w;
c) a surfactant at from about 0.01% to about 7% w/w;
d) a preservative at from about 0.001% to about 3% w/w; and
e) a pharmaceutically acceptable liquid carrier at from about 10% to about 95% w/w, wherein the suspension is free from xanthan gum and polyoxyethylene stearate.

In accordance with another embodiment of the present invention, there is provided an immediate release oral ready to use suspension for use in the treatment of seizures, partial onset seizures, epilepsy, neuropathic pain, migraine, fibromyalgia, trigeminal neuralgia, bipolar disorders, attention disorders, anxiety disorders, affective disorders, schizoaffective disorders, sensorimotor disorders, and vestibular disorders.

In accordance with another aspect of the present embodiment, there is provided a stable suspension comprising eslicarbazepine or its pharmaceutically acceptable salts, wherein the suspending agent is selected from gellan gum, sodium carboxymethylcellulose, a mixture of carboxymethylcellulose and microcrystalline cellulose, propylene glycol alginate and combinations thereof.

In accordance with another embodiment of the present invention, there is provided an immediate release oral ready to use suspension comprising (a) eslicarbazepine or its pharmaceutically acceptable salts, esters, hydrates or polymorphs thereof and (b) suspending agent, wherein the suspending agent is effective for maintaining a sedimentation volume ratio of more than about 0.8 for at least 10 hours after the suspension is prepared. In accordance with another embodiment of the present invention, the suspension maintains a sedimentation volume ratio of more than about 0.7, more than about 0.8, or more than about 0.9 for a period of at least about 10 hours, at least about 12 hours, at least about 15 hours, at least about 18 hours, at least about 20 hours, at least 1 day, at least 2 days, or at least 6 days after the suspension is prepared.

In accordance with another embodiment of the present invention, there is provided an immediate release oral ready to use suspension comprising (a) eslicarbazepine or its pharmaceutically acceptable salts, esters, hydrates or polymorphs thereof and (b) a suspending agent, wherein the ratio of eslicarbazepine:suspending agent ranges from 1:0.01 to 1:4 by weight. In another embodiment, the ratio of eslicarbazepine:suspending agent ranges from 1:0.05 to 1:1 by weight. In yet another embodiment, the ratio of eslicarbazepine:suspending agent ranges from 1:0.05 to 1:0.5 by weight.

In accordance with another embodiment of the present invention, there is provided an immediate release oral ready to use suspension comprising eslicarbazepine or its pharmaceutically acceptable salts, esters, hydrates or polymorphs thereof, wherein the suspension is bioequivalent to the marketed eslicarbazepine tablet (APTIOM®-Eslicarbazepine acetate Oral Tablets 200 mg, 400 mg, 600 mg and 800 mg).

In accordance with another embodiment of the present invention, there is provided an immediate release oral pharmaceutical ready to use suspension comprising eslicarbazepine or its pharmaceutically acceptable salts, esters, hydrates or polymorphs thereof, wherein the suspension exhibits a comparable dissolution compared to the commercially marketed tablet of eslicarbazepine (APTIOM®-Eslicarbazepine acetate Oral Tablets 200 mg, 400 mg, 600 mg and 800 mg).

In accordance with another embodiment of the present invention, there is provided an immediate release oral pharmaceutical ready to use suspension comprising eslicarbazepine or its pharmaceutically acceptable salts, esters, hydrates or polymorphs thereof, in which the bitter taste of eslicarbazepine is masked by one or more taste-masking agents.

In accordance with another embodiment of the present invention, there is provided an immediate release oral pharmaceutical ready to use suspension comprising eslicarbazepine or its pharmaceutically acceptable salts, esters, hydrates or polymorphs thereof, wherein the suspension is free of propylene glycol.

In accordance with another embodiment of the present invention, sucrose has a particle size such that not less than 90% particles are below 200 µm. In particular, sucrose has a particle size such that not less than 90% particles are below 100 µm. This helps in achieving improved uniformity of the drug in the mixture.

In accordance with other embodiment of the present invention, there is provided a stable suspension comprising about 0.01% to about 90% by weight of eslicarbazepine or its pharmaceutically acceptable salts, esters, hydrates or polymorphs thereof, preferably in the range of about 0.1% to about 40% by weight on the basis of the total weight of the composition.

In accordance with other embodiment of the present invention, there is provided a stable suspension comprising eslicarbazepine or its pharmaceutically acceptable salts, esters, hydrates or polymorphs thereof, wherein the amount of eslicarbazepine in the suspension ranges from about 0.1 mg/mL to about 400 mg/mL. The amount of eslicarbazepine in the suspension ranges preferably from about 0.5 mg/mL to 300 mg/mL, preferably from about 0.5 mg/mL to 200 mg/mL, preferably from about 0.5 mg/mL to 100 mg/mL. More preferably the amount of eslicarbazepine in the suspension ranges from about 0.5 mg/mL to 75 mg/mL.

In accordance with one aspect of the present embodiment, there is provided a stable suspension comprising eslicarbazepine or its pharmaceutically acceptable salts, esters, hydrates or polymorphs thereof, wherein the amount of eslicarbazepine in suspension is 1 mg/mL, 2 mg/5 mL, 5 mg/5 mL, 25 mg/5 mL, 50 mg/5 mL, 100 mg/5 mL and 250 mg/5 mL, 5 mg/mL, 25 mg/mL, 50 mg/mL, 100 mg/mL and 250 mg/mL. Particularly, the amount of eslicarbazepine in suspension is 50 mg/mL and 100 mg/mL.

In accordance with other embodiment of the present invention, there is provided a stable suspension comprising eslicarbazepine or its pharmaceutically acceptable salts, esters, hydrates or polymorphs thereof, wherein the pH of suspension is in range of 2 to 9. Preferably, the pH of the suspension is in a range of 2 to 8, and in a range of 3 to 8. More preferably, the pH of the suspension is in a range of 3.0 to 6.5 and in a range of 3.5 to 6.5. In accordance with other embodiment of the present invention, there is provided a stable suspension comprising eslicarbazepine or its pharmaceutically acceptable salts, esters, hydrates or polymorphs thereof, wherein the suspension is a liquid suspension packaged in a bottle.

In accordance with yet another embodiment of the present invention, there is provided a stable suspension comprising eslicarbazepine or its pharmaceutically acceptable salts, esters, hydrates or polymorphs thereof, wherein the suspension is a powder for suspension packaged in a bottle or sachet.

In accordance with yet another embodiment of the present invention, there is provided a suspension comprising eslicarbazepine or its pharmaceutically acceptable salts, esters, hydrates or polymorphs thereof, wherein the suspension is free of any sugar.

In accordance with yet another embodiment of the present invention, there is provided a suspension comprising eslicarbazepine or its pharmaceutically acceptable salts, esters, hydrates or polymorphs thereof, wherein the suspension is free of any dye.

In accordance with yet another embodiment of the present invention, there is provided a suspension comprising eslicarbazepine or its pharmaceutically acceptable salts, esters, hydrates or polymorphs thereof, wherein the suspension is free of any natural gum.

In accordance with yet another embodiment of the present invention, there is provided a suspension comprising eslicarbazepine or its pharmaceutically acceptable salts, esters, hydrates or polymorphs thereof, wherein the suspension is free of saccharin sodium.

In accordance with yet another embodiment of the present invention, there is provided a suspension comprising eslicarbazepine or its pharmaceutically acceptable salts, esters, hydrates or polymorphs thereof, wherein the suspension is free of xanthan gum, polyoxyethylene stearate and saccharin sodium.

In accordance with yet another embodiment of the present invention, there is provided a suspension comprising eslicarbazepine or its pharmaceutically acceptable salts, esters, hydrates or polymorphs thereof, wherein the suspension is administered at least once daily.

In accordance with yet another embodiment of the present invention, there is provided a suspension comprising eslicarbazepine or its pharmaceutically acceptable salts, esters, hydrates or polymorphs thereof, wherein the suspension contains bubble gum flavor, peppermint flavor, fantasy fruit masking flavor, strawberry flavor, or their combination as the flavoring agents.

In accordance with yet another embodiment of the present invention, there is provided a suspension comprising eslicarbazepine acetate, wherein the total impurities/related substances are not more than 2% when the suspension is stored at 40° C./75% R.H. for a period of at least 3 months.

In accordance with yet another embodiment of the present invention, there is provided a suspension comprising eslicarbazepine or its pharmaceutically acceptable salts, esters, hydrates or polymorphs thereof, wherein the suspension is provided in a kit comprising:
(a) an immediate release oral pharmaceutical ready to use suspension comprising eslicarbazepine; and
(b) a dosing syringe with a colored plunger and clear barrel for administering the suspension.

In accordance with yet another embodiment of the present invention, there is provided a suspension comprising eslicarbazepine or its pharmaceutically acceptable salts, esters, hydrates or polymorphs thereof, wherein the suspension is provided in a kit comprising:
(a) an immediate release oral pharmaceutical ready to use suspension comprising eslicarbazepine; and
(b) a dosing syringe with a colored plunger and clear barrel for administering the suspension,
wherein the suspension is free from xanthan gum and polyoxyethylene stearate.

According to another embodiment of the present invention, eslicarbazepine has a particle size distribution $D_{90}$ less than about 200 μm. Eslicarbazepine has a particle size distribution $D_{90}$ between 5 μm and 200 μm. Eslicarbazepine has a particle size distribution particularly $D_{90}$ between 5 μm and 175 μm, particularly $D_{90}$ between 5 μm and 150 μm, particularly $D_{90}$ between 5 μm and 125 μm, particularly $D_{90}$ between 5 μm and 100 μm, particularly $D_{90}$ between 5 μm and 75 μm, and particularly $D_{90}$ between 5 μm and 50 μm.

In accordance with one embodiment of the present invention, there is provided a process for the preparation of a stable suspension comprising eslicarbazepine or its pharmaceutically acceptable salts, esters, hydrates or polymorphs thereof, and one or more pharmaceutically acceptable excipients and/or a liquid carrier, wherein the process utilized is blending, dry granulation, wet granulation, spheronization extrusion process, hot melt extrusion process, homogenization or the like.

In accordance with one embodiment of the present invention, there is provided a process for preparation of a ready to use suspension, wherein the process comprises the following steps:
(i) dissolving/dispersing one or more pharmaceutically acceptable excipients in a portion of water;
(ii) dispersing eslicarbazepine or its pharmaceutically acceptable salts, esters, hydrates or polymorphs thereof in the solution/dispersion of step (i) to form a dispersion
(iii) mixing suspending agent in another portion of water;
(iv) adding the mixture of step (iii) to the dispersion of step (ii); and
(v) optionally adding one or more pharmaceutically acceptable excipients to the dispersion of step (iv); and
(vi) optionally homogenizing the mixture of step (iv) to form a suspension.

In accordance with one embodiment of the present invention, there is provided a process for preparation of a ready to use suspension, wherein the process comprises the following steps:
(i) mixing suspending agent, pH adjusting agent/buffering agent, sweetener, and preservative in a portion of a liquid carrier to form a dispersion;
(ii) mixing eslicarbazepine or its pharmaceutically acceptable salts, esters, hydrates or polymorphs thereof and surfactant in another portion of a liquid carrier to form a dispersion
(iii) adding the dispersion of step (ii) to the dispersion of step (i); and
(iv) adding one or more pharmaceutically acceptable excipients (sweetener, flavoring agent) to the dispersion of step (iii) and the remaining portion of the liquid carrier to form a suspension.

In accordance with other embodiment of the present invention, there is provided a process for preparation of a powder for suspension, wherein process comprises the following steps:
(i) mixing eslicarbazepine or its pharmaceutically acceptable salts, esters, hydrates or polymorphs thereof with one or more pharmaceutically acceptable excipients;
(ii) granulating the mixture of step (i) using a solvent;
(iii) drying the granulated mixture of step (ii);
(iv) milling the mixture of step (iii) to form granules; and
(v) mixing the granules of step (iv) optionally with one or pharmaceutically acceptable excipients to form the suspension powder for reconstitution.

In accordance with other embodiment of the present invention, there is provided a process for the preparation of a suspension powder for reconstitution, wherein process comprises the following steps:
(i) mixing eslicarbazepine or its pharmaceutically acceptable salts, esters, hydrates or polymorphs thereof with one or more pharmaceutically acceptable excipients;
(ii) compacting the mixture of step (i) to form slugs;
(iii) milling the slugs of step (ii) to form granules; and
(v) mixing the granules of step (iii) optionally with one or pharmaceutically acceptable excipients to form the suspension powder for reconstitution.

In accordance with other embodiment of the present invention, there is provided a process for the preparation of a suspension powder for reconstitution, wherein process comprises the following steps:
(i) mixing eslicarbazepine or its pharmaceutically acceptable salts, esters, hydrates or polymorphs thereof with one or more pharmaceutically acceptable excipients; and
(ii) optionally lubricating the mixture of step (i) to form the suspension powder for reconstitution.

Powder/granules for oral suspension can be reconstituted using water or powder/granules for oral suspension can be administered by sprinkling the powder/granules on one teaspoonful of apple sauce or empty granules into a small cup or teaspoon containing one teaspoon of apple juice.

The suspension of the present invention provides advantages such as absence of lumps even after long storage when the composition is shaken as well as good pourability. The suspension of the invention has good physical stability properties such as low level of sedimentation (reduced or no caking) and easy re-dispersion on agitation. Moreover, it provides dose uniformity during each administration.

In accordance with another embodiment of the present invention, there is provided a ready to use liquid suspension comprising eslicarbazepine or its pharmaceutically acceptable, salts, esters hydrates or polymorphs thereof and at least one or more pharmaceutically acceptable excipient and/or a liquid carrier comprising suspending agent, antioxidant, anticaking agent, antifoaming agent, pH adjusting agent, sweetening agent, flavoring agent, surfactant/wetting agent, buffer, and preservative wherein, the suspension is easily dispersible or re-suspendable in a pharmaceutically acceptable liquid carrier including aqueous and/or non-aqueous carrier.

In accordance with still another embodiment of the present invention, there is provided a stable suspension comprising eslicarbazepine or its pharmaceutically acceptable salts, esters, hydrates or polymorphs thereof, wherein the composition is substantially free from other polymorphic forms.

In accordance with still another embodiment of the present invention, there is provided a suspension comprising eslicarbazepine or its pharmaceutically acceptable salts, esters, hydrates or polymorphs thereof in an amount of about 0.01% to about 90% by weight wherein, the composition exhibits desirable technical attributes like pourability, viscosity, dissolution, stability, re-suspendability and re-dispersibility.

In accordance with still another embodiment of the present invention, there is provided a kit comprising:
(a) an immediate release oral pharmaceutical suspension dosage form comprising eslicarbazepine or its pharmaceutically acceptable salts, esters, hydrates or polymorphs thereof with one or more pharmaceutically acceptable excipients and/or carrier,
(b) a dispensing and/or dosing syringe for administering the composition, and
(c) optionally, instructions for preparation and use.

In accordance with still another embodiment of the present invention, there is provided a kit comprising:
(a) an immediate release oral pharmaceutical suspension dosage form comprising eslicarbazepine or its pharmaceutically acceptable salts, esters, hydrates or polymorphs thereof with one or more pharmaceutically acceptable excipients and/or carrier,
(b) a dispensing and/or dosing syringe or a measuring cup for administering the composition, and
(c) optionally, instructions for preparation and use.

In accordance with still another embodiment of the present invention, there is provided a kit comprising:
(a) an immediate release oral pharmaceutical suspension dosage form comprising eslicarbazepine or its pharmaceutically acceptable salts, esters, hydrates or polymorphs thereof with one or more pharmaceutically acceptable excipients and/or carrier,
(b) a measuring cup for administering the composition, and
(c) optionally, instructions for preparation and use.

In another embodiment the liquid composition of the present invention includes particle size of eslicarbazepine or its pharmaceutically acceptable esters, salts, solvates, polymorphs, enantiomers or mixtures thereof, having a particle size distribution such that $D_{90}$ is less than about 200 μm, $D_{50}$ is less than about 100 μm and $D_{10}$ is less than about 50 μm. Particularly, $D_{50}$ is between about 5 μm to about 100 μm. The particle size of eslicarbazepine can be measured by suitable techniques such as Laser light scattering (e.g. Malvern Light Scattering), Coulter counter, microscopy, Fraunhofer diffraction and any other technique known in the art.

In another embodiment of the present invention there is provided a suspension powder for reconstitution comprising eslicarbazepine or its pharmaceutically acceptable esters, salts, solvates, polymorphs, enantiomers or mixtures thereof, present in an amount of more than 0.01% by weight based on the total weight of the composition with one or more pharmaceutically acceptable excipient and/or a liquid carrier such as suspending agent, antioxidant, anticaking agent, antifoaming agent, pH adjusting agent, sweetening agent, flavoring agent, solubilizer/wetting agent, buffer, preservative, aqueous or non-aqueous carrier and the like.

Carrier/vehicle/solvent used in the suspension of the present invention include aqueous and non-aqueous carrier but are not limited to water, alcohol, polyethylene glycol, propylene glycol or glycerin, buffers, oil, or combinations thereof. Oils include peanut oil, soy bean oil, corn oil, sesame oil, cottonseed oil, acetylated glycerides, ethyl oleate, mineral oil, fatty acid esters, mono- or di-fatty acid esters of polyethylene glycols, or glyceryl mono-oleate. Particularly, the suspensions are aqueous based. By "aqueous carrier" is meant a suspension comprising water, or a combination of water and a water-miscible organic solvent or solvents. Water-miscible solvents include but are not limited to propylene glycol, polyethylene glycol and ethanol. By "non-aqueous carrier" is meant a suspension in which the carrier does not include water. The carrier can also include one more pharmaceutically acceptable excipients which can be in dissolved or dispersed form. In particular, the carrier is water or a combination of water and glycerin. The carrier is present in an amount from about 5% w/w to about 99% w/w, about 10% w/w to about 99% w/w, particularly from about 30% w/w to about 95% w/w, particularly from about 40% w/w to about 95% w/w, particularly from about 50% w/w to about 95% w/w and particularly from about 60% w/w to about 95% w/w.

The viscosity agent/suspending agent enhances the physical stability of the composition by sufficiently increasing the viscosity to retard the settling rate, yet allowing adequate pourability. They also allow the product to be easily resuspendable so that an appropriate dose can be delivered with minimal shaking. Suitable thickening agents/viscosity agents/suspending agents are selected from the group comprising cellulose derivatives such as hydroxyethyl cellulose, hydroxypropyl cellulose, hydroxypropylmethyl cellulose, methylcellulose, carboxymethyl cellulose and its salts/derivatives e.g., carboxymethyl cellulose sodium, microcrystalline cellulose, and co-processed spray dried forms of microcrystalline cellulose and carboxymethyl cellulose sodium (such as AVICEL® RC-501, AVICEL® RC-581, AVICEL® RC-591, and AVICEL® CL-611); carbomers (such as those available under the trade name CARBOPOL®); gums such as locust bean gum, tragacanth gum, arabinogalactan gum, agar gum, gellan gum, guar gum, apricot gum, karaya gum, sterculia gum, acacia gum, gum arabic, and carrageenan; pectin; propylene glycol alginate, dextran; gelatin; polyethylene glycols; polyvinyl compounds such as polyvinyl acetate, polyvinyl alcohol, and polyvinyl pyrrolidone; sugar alcohols such as xylitol and mannitol; colloidal silica; maltodextrin, starch; and mixtures thereof. The liquid compositions of the present invention are free of xanthan gum. In a preferred embodiment, the suspending agent is a co-processed spray dried form of microcrystalline cellulose and carboxymethyl cellulose sodium.

The suspending agents/viscosity agents are present in an amount of about 0.01% to about 20% w/w of the composition. Particularly, the viscosity agents are present in an amount of about 0.01% to about 10% w/w of the composition. More particularly, the viscosity agents are present in an amount of about 0.1% to about 5% w/w of the composition. Much more particularly, the viscosity agents are present in an amount of about 0.1% to about 3% w/w of the composition.

The suspension is easily pourable and when shaken has a viscosity in the range of 100 to 5000 cps at 25° C. Particularly, the viscosity is in the range of 100 to 2500 cps at 25° C. Particularly, the viscosity is in the range of 100 to 1500 cPs at 25° C. More particularly, the viscosity is in the range of 700-1200 cps at 25° C.

The term "shaken" as used herein refers to shaken prior to use, e.g. by a patient or pharmacist, e.g. vigorously shaken, e.g. by hand, e.g. for at least 5 to 40 seconds.

The viscosity can be measured by using a suitable instrument such as Brookfield viscometer and Haake VT 550 viscometer at room temperature (25° C.).

Diluents or fillers are substances which usually provide bulk to the composition. Various useful fillers or diluents include, but are not limited to sucrose, sugar alcohols, sorbitol, xylitol, erythritol, starch, pregelatinized starch, calcium carbonate, calcium phosphate, dibasic anhydrous, calcium phosphate, dibasic dihydrate, calcium phosphate tribasic, calcium sulphate, cellulose powdered, silicified microcrystalline cellulose, cellulose acetate, lactose, magnesium carbonate, magnesium oxide, maltodextrin, mannitol, microcrystalline cellulose, silicified microcrystalline cellulose polydextrose, sodium alginate, sodium chloride and or mixtures thereof. Preferably the diluent used is sucrose or a sugar alcohol. The diluent is present in an amount of 5 to 98% w/w of the total composition.

The amount of surfactant or wetting agent should be sufficient to facilitate the dispersion of eslicarbazepine in the suspension. At the same time, it should provide improved wettability of the eslicarbazepine acetate. Suitable surfactant or wetting agents are selected from the group comprising non-ionic, anionic, cationic, or zwitterionic surfactants, and combinations thereof. Suitable examples of wetting agents are sodium lauryl sulphate; cetrimide; polyethylene glycols; polyglycerin fatty acid esters such as decaglyceryl monolaurate and decaglyceryl monomyristate; sorbitan fatty acid esters such as sorbitan monostearate; polyoxyethylene sorbitan fatty acid esters such as polyoxyethylene sorbitan monooleate; polyoxyethylene alkyl ether such as polyoxyethylene lauryl ether; polyoxyethylene castor oil; polyoxyethylene-polyoxypropylene block copolymers such as poloxamers (e.g. Poloxamer 188); and combinations thereof. Particularly, surfactants or wetting agents are non-ionic. The liquid compositions of the present invention are free of polyoxyethylene stearate such as polyoxy 100 stearate (MYRJ® 59P) as the wetting agent. The surfactant or wetting agents are present in an amount of about 0.01% to about 7% w/w of the composition. Particularly, the surfactant or wetting agents are present in an amount of about 0.01% to about 3% w/w, and more particularly from about 0.01% to about 1% w/w of the composition.

Various useful preservatives include, but are not limited to, parabens such as methylparaben, propylparaben, butyl paraben and their salts, sorbic acid, sodium sorbate, potassium sorbate, calcium sorbate, benzoic acid, sodium benzoate, potassium benzoate, calcium benzoate, methyl hydroxybenzoate, ethyl para-hydroxybenzoate, sodium ethyl para-hydroxybenzoate, sodium metabisulphite, chlorhexidine, diazolidinyl urea, sodium citrate, butylated hydroxyl toluene (BHT), butylated hydroxyl anisole (BHA), tocopherol, ethylenediamine tetraacetic acid, propyl gallate, quaternary compounds, e.g. benzalkonium chloride and cetylpyridinium chloride, phenyl ethyl alcohol and combinations thereof. In particular, the preservative is selected from benzoic acid and its salts and parabens. The preservative is present in an amount of about 0.001% w/w to about 4% w/w of the composition, particularly in an amount of about 0.001% w/w to about 3% w/w of the composition.

Anticaking agent helps to improve the re-suspendability of the formulation. Various useful Anticaking agents include, but are not limited to, colloidal silica and/or colloidal silicon dioxide, calcium phosphate tribasic, magnesium oxide, magnesium silicate, calcium silicate and combinations thereof. The anticaking agents are present in an amount of about 0.1% to about 10% w/w of the composition. More particularly, the anticaking agents are present in an amount of about 0.5% to about 7% w/w of the composition.

Various useful antioxidants include, but are not limited to, ascorbic acid, tert-butylhydroquinone, sodium pyrosulfite, glutathione, sodium bisulfite, sodium sulfite, a-tocopherol, a-tocopherol acetate, monothioglycerol, cysteine, ascorbyl palmitate, acetylcysteine, dithiothreitol, sodium metabisulfite, thiourea, sodium thiosulfate, butylated hydroxy anisole (BHA), butylated hydroxytoluene (BHT) and propyl gallate. The antioxidants are present in an amount of 0% to about 10% w/w of the composition.

Various useful sweetening agents include, but are not limited to, sugars such as sucrose, dextrose, fructose, lactose, maltose, invert sugar; sugar alcohols such as sorbitol, mannitol, xylitol, lactitol, erythritol, maltodextrin, maltitol, isomaltitol, isomalt, maltulose, isomaltulose, lactulose, threitol, arabitol, ribitol, galactitol, and sugar substitutes such as saccharin sodium, aspartame, thaumatin, acesulfame, combinations thereof. Sugar or a sugar alcohol can also act as filler. Preferably sweetening agent used is sodium saccharin. The sweetening agents are present in an amount of about 0.01% w/w to about 99% w/w of the composition, particularly in an amount of about 0.1% w/w to about 90% w/w of the composition, particularly in an amount of about 0.01% w/w to about 80% w/w of the composition, particularly in an amount of about 0.1% w/w to about 80% w/w of the composition, particularly in an amount of about 0.1% w/w to about 70% w/w of the composition, particularly in an amount of about 0.1% w/w to about 60% w/w of the composition, particularly in an amount of about 0.1% w/w to about 50% w/w of the composition, particularly in an amount of about 0.1% w/w to about 40% w/w of the composition and more particularly in an amount of about 0.1% w/w to about 30% w/w of the composition. Thaumatin or a combination of sorbitol and thaumatin as the sweetening agent is preferable.

Various useful flavoring agents, include, but are not limited to, flavors such as banana, lemon, orange, grape, lime and grapefruit, vanilla, bubble gum, peppermint, fantasy fruit masking flavor (as commercially available), and fruit essence, including apple, banana, pear, peach, strawberry, raspberry, cherry, plum, pineapple, apricot; synthetic flavor oils and flavoring aromatics and/or natural oils, extracts from plant leaves, flowers, fruits such as cinnamon oil, oil of wintergreen, peppermint oils, clove oil, citrus oil, bay oil, anise oil, eucalyptus, thyme oil, cedar leaf oil, oil of nutmeg, oil of sage, oil of bitter almonds, and cassia oil; maltol, ethyl vanillin, menthol, citric acid, fumaric acid, ethyl maltol, and tartaric acid and combinations thereof. The flavoring agents are present in an amount of about 0.01% to about 7% w/w of the composition. Particularly, the flavoring agents are present in an amount of about 0.01% to about 5% w/w of the composition, about 0.01% to about 3% w/w of the composition about 0.01% to about 2% w/w of the composition and particularly from about 0.01% to about 1% w/w of the composition.

Various useful isotonicity adjusting agent include, but are not limited to, sodium chloride, mannitol, D-sorbitol, glucose, glycerin or the like.

Various useful pH adjusting agent or buffering agents include, but are not limited to, citrate buffers, phosphate buffers, or any other suitable buffer known in the art including monosodium dibasic phosphate, gluconic acid, lactic acid, citric acid, trisodium citrate, acetic acid, maleic acid, tartaric acid, fumaric acid, sodium phosphate, sodium gluconate, sodium lactate, sodium citrate, sodium acetate potassium citrate, sodium bicarbonate, potassium bicarbonate, sodium dihydrogen phosphate and potassium dihydrogen phosphate, and combinations thereof. They also include combination of acidic and basic substances. Strong acids such as hydrochloric acid, sulfuric acid, phosphoric acid and the like can be used alone or in combination with basic substance such as inorganic bases (e.g., sodium hydroxide, potassium hydroxide, sodium carbonate, sodium hydrogen carbonate, magnesium carbonate, calcium carbonate, magnesium oxide, ammonia, synthetic hydrotalcite), organic bases (e.g., basic amino acid such as lysine, arginine, etc., meglumine, and the like).

The pH adjusting agent or buffering agents are present in an amount of about 0.001% to about 15% w/w of the composition, particularly from about 0.01% to about 10% w/w of the composition, from about 0.01% to about 8% w/w of the composition, from about 0.01% to about 5% w/w of the composition, particularly from about 0.01% to about 3% w/w of the composition and particularly from about 0.005% to about 3% w/w of the composition. In particular, citrate and trisodium citrate buffer is used. The pH of the eslicarbazepine suspension ranges from about 2 to about 8. Preferably, the pH of the eslicarbazepine suspension ranges from 3.0 to 6.5. In an embodiment, the buffer concentration is in the range of about 0.5 mM to about 40 mM. Particularly, the buffer concentration is in the range of about 2 mM to about 20 mM.

Various useful taste masking agents include, but are not limited to, water soluble and/or insoluble polymeric excipient, water insoluble non-polymeric excipient, adsorbent, ion exchange resins such as AMBERLITE® (ion exchange resins), AMBERLITE® CG 50 (weakly acidic, carboxylic acid type of cation exchange resin), AMBERLITE® IRP-64 (cationic ion exchange resin that is derived from a copolymer of methcrylic acid and divinyl benzene), AMBERLITE® IRP-69 (sodium polystyrene sulfonate or sulfonated copolymer of styrene and divinylbenzene), INDION® 204 (crosslinked polyacrylic acid), INDION® 214 (crosslinked polyacrylic acid), INDION® 234 (crosslinked polyacrylic acid), INDION® CRP 244 (Polystyrene matrix cation-exchange resins), INDION® CRP 254 (Polystyrene matrix cation-exchange resins), carbomers such as Carbomer 934, Carbomer 974, Carbomer 971, PEG-5M, CARBOPOL® 934P NF (Carbomer 934P, NF), CARBOPOL® 971P (Carbomer 971P, NF), CARBOPOL® 974P NF (Carbomer 974P, NF), alkali metal chlorides or an alkaline earth metal chloride or a derivative thereof, OPADRY®AMB (polyvinyl alcohol or copolymers or mixtures thereof—a water soluble coating material available from Colorcon, Pa., USA), sodium starch glycolate, Bitter Masker US 151 flavor, PEG-5M, sodium acetate, ethylcellulose, cyclodextrin, beta-cyclodextrin, polyvinyl acetate dispersion, trehalose, vinylacetate, polystyrene, cellulose acetate butyrate, methacrylic acid, and methyl methacrylates such as EUDRAGIT® R) L100, polymethacrylates (such as EUDRAGIT® (R) L100), sodium chloride, polyethoxylated castor oil, KOLLIPHOR® RH 40 (Polyoxyl 40 hydrogenated castor oil), SENTRY® POLYOX® WSR N80 NF (poly (ethylene oxide)), natural or synthetic fatty type or other flavorant such as cocoa, chocolate (especially mint chocolate), cocoa butter, milk fractions, vanillin butterfat, egg or egg white, peppermint oil, wintergreen oil, spearmint oil, and similar oils. Compounds which reduce throat catch include for example high solubility acids include amino acids (eg alanine, arginine etc), glutaric, ascorbic, malic, oxalic, tartaric, malonic, acetic, citric acids, low solubility acids include oleic, stearic, and aspartic acids plus certain amino acids such as glutamic acid, glutamine, histidine, isoleucine, leucine, methionine, phenylalanine, serine, tryptophan, tyrosine, valine, and fumaric acid. The taste-masking agents are present in an amount of about 0.01% to about 50% w/w of the composition, particularly from about 0.01% to about 30% w/w of the composition, particularly from about 0.01% to about 20% w/w of the composition, and particularly from about 0.01% to about 10% w/w of the composition.

Various useful antifoaming agents include, but are not limited to simethicone.

The pharmaceutical composition of the present invention can be packaged in a suitable pack/container such as amber colored polyethylene terephthalate (PET) bottle, glass bottle, high density polyethylene (HDPE) bottle, low density polyethylene (LDPE) bottle, polypropylene (PP) bottle, packets, pouches, sachets and the like. The glass or plastic bottle is provided with a child proof closure. The package can include a syringe, dosing syringe or dispensing syringe or measuring cup or any combination (marked in mL) for ease of dosing. The container(s) of the present invention may have a syringe or cup adapted to be attached to the container. The syringe or cup as per the present invention can be of material such as polyethylene terephthalate (PET), glass, high density polyethylene (HDPE), low density polyethylene (LDPE), polypropylene (PP) or any other material known in the art.

The container such as bottle has a fill volume of, e.g., from about 50 mL to about 500 mL comprising eslicarbazepine suspension. Packs chosen are made of material which is non-reactive with the suspension and suspension powder for reconstitution. Containers for use in the storage of the oral suspensions may be used to administer a multiple dose of eslicarbazepine.

The liquid pharmaceutical composition of the present invention can be used for treatment of seizures, partial onset seizures, epilepsy, neuropathic pain, migraine, fibromyalgia, trigeminal neuralgia, bipolar disorders, attention disorders, anxiety disorders, affective disorders, schizoaffective disorders, sensorimotor disorders, and vestibular disorders.

The compositions of the present invention are for oral administration. The compositions may be taken in measured doses using a container, cup, straw, spoon, syringe, dispensing syringe, dosing syringe or any other suitable device. The compositions may be provided in liquid form, or in dry form (such as granule or powder or multiparticulate) to which water or liquid solvent or diluent is added to provide a liquid composition of this invention. Ingredients suitable for liquid compositions are known and such compositions may be made by methods known in the art. In an embodiment, the syringe, dispensing syringe or dosing syringe or combination thereof are used to transfer a predetermined amount of the composition comprising eslicarbazepine or its salt thereof, into the patient's mouth. In an embodiment, the measuring cup is used to measure the dose as per patient's requirement so that a precise dosage can be obtained for oral administration.

Suitable coloring agents are selected from the group comprising FD&C (Federal Food, Drug and Cosmetic Act) approved coloring agents; natural coloring agents; natural juice concentrates; pigments such as iron oxide, titanium dioxide, and zinc oxide; and combinations thereof.

The suspensions of the present invention are homogenous and deliver the desired dose of eslicarbazepine in every use without any risk of overdosing or underdosing. The compositions provide predictable eslicarbazepine release throughout the shelf life.

The invention may be further illustrated by the following examples, which are for illustrative purposes only and should not be construed as limiting the scope of the invention in any way.

EXAMPLES

Example 1—Ready to Use Suspension

| Ingredients | Quantity (% w/w) |
|---|---|
| Eslicarbazepine acetate | 6.70 |
| Sucrose | 26.80 |
| Sorbitol | 40.20 |
| Poloxamer 188 | 1.10 |
| Propylene glycol | 15.01 |
| Polysorbate 80 | 4.70 |
| Citric acid | 0.06 |
| Monosodium dibasic phosphate | 0.03 |
| Sodium saccharin | 0.08 |
| Methyl paraben | 0.16 |
| Propyl paraben | 0.11 |
| Avicel® RC591 (Microcrystalline cellulose and sodium carboxymethylcellulose)/Sodium carboxymethylcellulose | 0.89 |
| Acesulfame potassium | 1.61 |
| Bubble gum flavor | 0.04 |
| Purified water | q.s. |

Procedure:

1. Polysorbate 80 and eslicarbazepine acetate were mixed.
2. Propylene glycol and Poloxamer 188 were added to step 1 and mixed.
3. Sodium saccharin, mono sodium dibasic phosphate anhydrous and citric acid were added to purified water to form a solution.
4. Methyl paraben and propyl paraben were added to propylene glycol to obtain a clear solution.
5. AVICEL® RC 591 (Microcrystalline cellulose and sodium carboxymethylcellulose)/sodium carboxymethylcellulose was added to water.
6. Solution of step 3 was added to step 2 and mixed.
7. Solution of step 4 was added to step 6 and mixed.
8. Dispersion of step 5 was added to step 7 and mixed.
9. Sucrose, sorbitol, acesulfame potassium, and bubble gum flavor were added to water and mixed with the mixture of step 8 and homogenized.

Examples 2-6—Suspension Powder for Reconstitution

| | Quantity (% w/w) | | | | |
|---|---|---|---|---|---|
| Example | 2 | 3 | 4 | 5 | 6 |
| Eslicarbazepine acetate | 12.50 | 12.50 | 12.50 | 12.50 | 12.50 |
| Sucrose | 86.30 | 79.60 | 79.53 | 78.72 | 78.48 |
| Polysorbate 80 | — | — | 0.08 | — | — |
| Citric acid | 0.11 | 0.11 | 0.11 | 0.11 | — |
| Monosodium dibasic phosphate | 0.06 | 0.06 | 0.06 | 0.06 | — |
| Tribasic sodium phosphate | — | — | — | — | 0.11 |
| Sodium saccharin | — | 0.15 | 0.15 | 0.15 | 0.15 |
| Sodium benzoate | — | 0.30 | 0.30 | 0.30 | 0.30 |
| Avicel® RC591 (Microcrystalline cellulose and sodium carboxymethylcellulose) | 0.88 | 0.88 | 0.88 | — | 1.75 |
| Silicon dioxide | — | 6.25 | 6.25 | 6.25 | 6.25 |
| Propylene glycol alginate | — | — | — | 1.75 | — |
| Gellan gum | — | — | — | — | 0.3 |
| Banana flavor/Cherry flavor | 0.16 | 0.16 | 0.16 | 0.16 | 0.16 |

Procedure:

1. Eslicarbazepine acetate and sucrose were mixed.
2. Tribasic sodium phosphate/sodium saccharin/sodium benzoate/Polysorbate 80 were dissolved in water.
3. The mixture of step 1 was granulated with the solution of step 2.
4. The wet mass of step 3 was dried and milled to form granules.
5. Remaining excipients were added to the granules of step 4 and mixed.

The suspension powder for reconstitution is reconstituted with a suitable carrier when required.

Examples 7-10—Ready to Use Suspension of Eslicarbazepine Acetate

| | | Quantity (% w/w) | | | |
|---|---|---|---|---|---|
| Ingredients | Function | Example 7 | Example 8 | Example 9 | Example 10 |
| Eslicarbazepine acetate | Active | 0.5-40 | 10 | 5 | 10 |
| Polysorbate 80 | Surfactant | 0.01-7 | 0.04 | 0.06 | 0.05 |
| Avicel® RC591 (Microcrystalline cellulose and sodium carboxymethylcellulose) | Suspending agent | 0.01-10 | 1.25 | 2.75 | 2.25 |
| Sorbitol | Sweetener | 1-70 | 10 | 15 | 20 |
| Thaumatin | Sweetener | 0.01-2 | 0.2 | 0.09 | 0.15 |
| Methyl paraben or propyl paraben or combination thereof | Preservative | 0.01-3 | 0.25 | 0.25 | 0.40 |
| Citric acid | Buffering agent | 0.01-5 | 0.10 | 0.07 | 0.05 |
| Trisodium citrate | Buffering agent | 0.01-5 | 0.15 | 0.08 | 0.05 |
| Lemon flavor or vanilla flavor or peppermint flavor or fantasy fruit masking flavor or strawberry flavor or bubble gum | Flavoring agent | 0.01-3 | 0.32 | 0.18 | 0.08 |

-continued

| Ingredients | Function | Quantity (% w/w) | | | |
|---|---|---|---|---|---|
| | | Example 7 | Example 8 | Example 9 | Example 10 |
| flavor or combinations thereof | | | | | |
| Glycerin | Carrier | 2-50 | 10 | 15 | 20 |
| Purified water | Carrier | q.s. | q.s | q.s | q.s |

Procedure

1. Sorbitol, AVICEL® RC591, citric acid and trisodium citrate were added to water with stirring to form a dispersion;

2. Methyl paraben and propyl paraben were added to glycerin with stirring;

3. Dispersion of step 2 was added to the dispersion of step 1 with stirring;

4. Eslicarbazepine acetate and polysorbate 80 were added to water with stirring and optionally homogenized;

5. Dispersion of step 4 were added to the dispersion of step 3; and

6. Thaumatin and flavoring agents were added to the dispersion of step 5 and the remaining amount of water is added to form the suspension.

Assay of Eslicarbazepine

The suspension powder for reconstitution of Examples 1, 2 and 6 were analyzed for drug content by HPLC method using C18 column (150×4.6 mm, 5 μm) using acetonitrile:water (50:50) at 215 nm. The results are provided in Table 1.

TABLE 1

| Assay for Eslicarbazepine | |
|---|---|
| Composition | % Assay |
| Example 1 | 102.9 |
| Example 2 | 99.7 |
| Example 6 | 101.70 | pH data: pH values were determined using potentiometry using USP <791> with the results provided in Table 2.

TABLE 2

| pH Value | |
|---|---|
| Composition | pH |
| Example 1 | 5.40 |
| Example 2 | 5.20 |
| Example 3 | 4.83 |
| Example 4 | 5.43 |
| Example 5 | 4.72 |
| Example 6 | 7.80 |
| Example 8 | 4.77 |

Dissolution Studies

The powders for suspension of Examples 1-6 were evaluated for in-vitro eslicarbazepine release. The in-vitro dissolution was determined using a USP type II apparatus (paddle) at 100 rpm in 1000 mL of acetate buffer (pH 4.5) at 37±0.5° C. by HPLC method. The results are reported in Table 3.

TABLE 3

Percentage (%) of the In-Vitro Eslicarbazepine Release in USP type II apparatus at 100 rpm in 1000 mL of acetate buffer (pH 4.5)
Percentage of Eslicarbazepine Release

| Time (minutes) | Example 1 | Example 2 | Example 3 | Example 4 | Example 5 | Example 6 |
|---|---|---|---|---|---|---|
| 15 | 102 | 72 | 107 | 110 | 103 | 96 |
| 30 | 101 | 84 | 109 | — | 104 | 98 |
| 45 | 100 | 89 | 109 | — | 104 | 99 |

Viscosity: The viscosity of the eslicarbazepine suspension of Example 8 was determined to be 321 cps using Brookfield viscometer using spindle LV-3 (Spindle number 63) at 50 rpm and 25° C.

Sedimentation Ratio

The sedimentation ratio was determined for Example 8 and the results are provided in Table 4. To measure the sedimentation ratio, the eslicarbazepine suspension of Example 8 was filled up to 100 mL in a 100 mL measuring cylinders and covered with a stopper. The initial height of the sediment was measured as $H_0$. After a particular time period (such as 1 day), measure the height of sediment as Hu. Table 4 reports the sedimentation ratio of eslicarbazepine suspension after 6 days. There is no change in the sedimentation ratio for at least 6 days. The sedimentation ratios of 1 at days 1 and 6 indicate that the suspension is physically stable.

Sedimentation ratio=$Hu/H_0$

TABLE 4

| | Sedimentation ratio | |
|---|---|---|
| | Sedimentation ratio | |
| Composition | 1 day | 6 days |
| Example 8 | 1 | 1 |

Dissolution Data

The eslicarbazepine suspension of Example 8 was evaluated for in-vitro eslicarbazepine release. The in-vitro dissolution was determined using a USP type II apparatus at 100 rpm in 1000 mL of acetate buffer (pH 4.5) at 37±0.5° C. by a validated HPLC method. The results are reported in Table 5.

TABLE 5

Percentage (%) of the In-Vitro Eslicarbazepine Release in USP type II apparatus at 100 rpm in 1000 mL of acetate buffer (pH 4.5)
Percentage of Eslicarbazepine Release

| Time (minutes) | Example 8 |
|---|---|
| 5 | 96 |
| 10 | 97 |
| 15 | 98 |
| 30 | 98 |

X-Ray Diffraction Study

Example 11—Ready to Use Suspension of Eslicarbazepine Acetate

| Ingredients | % w/w |
|---|---|
| Eslicarbazepine acetate | 10.00 |
| Polysorbate 80 | 0.04 |
| Microcrystalline cellulose and sodium carboxymethylcellulose | 2.00 |
| Sorbitol | 10.00 |
| Thaumatin | 0.15 |
| Methyl paraben/propyl paraben/ combination thereof | 0.25 |
| Citric acid | 0.10 |
| Trisodium citrate | 0.15 |
| Lemon flavor or peppermint flavor or fantasy fruit masking flavor or combinations thereof | 0.09 |
| Glycerin | 10.00 |
| Purified water | q.s |

Bruker D8 Advance X-Ray diffractometer with a CuKα radiation was used for X-Ray diffraction study of eslicarbazepine acetate suspension. FIG. 1 shows an overlay of eslicarbazepine acetate drug substance and eslicarbazepine suspension (initial) and eslicarbazepine suspension stability samples (stored at 80° C. for 5 days) as per Example 11.

The peaks of eslicarbazepine acetate API was observed in eslicarbazepine suspension samples (initial and stability sample stored at 80° C. for 5 days) at 5.58°, 9.82°, 11.07°, 12.63°, 17.80°, 19.33°, and 21.91±0.2° 2θ. Eslicarbazepine acetate was found to be stable in the suspension as no change in the XRD pattern of eslicarbazepine acetate was observed in the formulation.

Stability Studies

1. Stability Study of Eslicarbazepine Suspension of Example 8

Eslicarbazepine suspension prepared as per Example 8 was packed in a glass bottle and subjected to accelerated stability conditions 40° C./75% Relative Humidity (R.H.) and at 25° C./60% R.H. for 1 month. The results are provided in Table 6.

TABLE 6

Stability data of eslicarbazepine suspension of Example 8

| Test Parameter | Initial | 40° C./75% R.H., 1 month | 25° C./60% R.H., 1 month |
|---|---|---|---|
| pH | 4.77 | 4.69 | 4.67 |
| Viscosity | 321 | 370 | 351 |
| Related substances (R.S.) | 0.035 | 0.05 | 0.04 |
| Assay | 101.5 | 101.5 | 101.0 |

Dissolution (pH 4.5 acetate buffer, paddle, 1000 ml, 100 rpm)

| Time (minutes) | Percentage of Eslicarbazepine Release | | |
|---|---|---|---|
| 5 | 96 | 95 | 95 |
| 10 | 97 | 97 | 98 |
| 15 | 98 | 97 | 101 |
| 30 | 98 | 99 | 100 |

From the above data, it is clear that eslicarbazepine suspension is stable in a glass bottle when stored at 40° C./75% R.H. and 25° C./60% R.H. for a period of at least 1 month. Further, no phase separation was observed at these stability conditions.

2. Stability Study of Eslicarbazepine Suspension of Example 12

Eslicarbazepine suspension prepared as per Example 12 was packed in glass bottle and PET bottle and subjected to accelerated stability conditions 40° C./75% Relative Humidity (R.H.) for 1 month and 3 months and at 25° C./60% R.H. The results are provided in Table 7.

Example 12—Ready to Use Suspension of Eslicarbazepine Acetate

| Ingredients | % w/w |
|---|---|
| Eslicarbazepine acetate | 5.00 |
| Polysorbate 80 | 0.04 |
| Microcrystalline cellulose and sodium carboxymethylcellulose | 3.00 |
| Sorbitol | 20.00 |
| Sucralose | 1.00 |
| Methyl paraben or propyl paraben or combination thereof | 0.25 |
| Citric acid | 0.02 |
| Trisodium citrate | 0.03 |
| Orange flavor | 0.30 |
| Glycerin | 10.00 |
| Purified water | q.s |

TABLE 7

Stability data eslicarbazepine suspension of Example 12

| | Pack | | | | | | |
|---|---|---|---|---|---|---|---|
| | Glass Bottle | | | | PET Bottle | | |
| | | 40° C./75% R.H. | | 25° C./60% R.H. | 40° C./75% R.H. | | 25° C./60% R.H. |
| Condition | Initial | 1 month | 3 months | 3 months | 1 month | 3 months | 3 months |
| Related substances (R.S.) | 0.05 | 0.14 | 0.27 | 0.06 | 0.13 | 0.25 | 0.06 |

TABLE 7-continued

Stability data eslicarbazepine suspension of Example 12

Dissolution (pH 4.5 acetate buffer, paddle, 1000 ml 100 rpm)

| Time (minutes) | Percentage of Eslicarbazepine Release | | | | | | |
|---|---|---|---|---|---|---|---|
| 5  | 99  | 99 | 99 | 98 | 98 | 96 | 100 |
| 10 | 99  | 99 | 99 | 98 | 98 | 96 | 100 |
| 15 | 100 | 99 | 99 | 98 | 98 | 96 | 100 |
| 30 | 99  | 99 | 99 | 98 | 98 | 96 | 100 |

The undesirable known Related substances (R.S.)/impurities in eslicarbazepine acetate comprises oxcarbazepine, carbamazepine and dehydro eslicarbazepine and unknown impurities.

From the above data, it is clear that eslicarbazepine suspension is stable in glass bottle and PET bottle when stored at 40° C./75% R.H. and 25° C./60% R.H. for a period of at least 3 months. Further, no phase separation was observed at these stability conditions.

pH Stability Profile pH stability profile of the ready to use suspension of eslicarbazepine acetate of Example 13 was studied. The data is represented in Table 8.

Example 13—Ready to Use Suspension of Eslicarbazepine Acetate

| Ingredients | Quantity (% w/w) |
|---|---|
| Eslicarbazepine acetate | 5.00 |
| Polysorbate 80 | 0.04 |
| Avicel® RC591 (Microcrystalline cellulose and sodium carboxymethylcellulose) | 2.75 |
| Sorbitol | 20.00 |
| Methyl paraben or propyl paraben or combinations thereof | 0.25 |
| Citric acid | 0.04 |
| Trisodium citrate | 0.02 |
| Glycerin | 10.00 |
| Purified water | q.s. |

TABLE 8 pH stability profile of eslicarbazepine suspension

| Related substances | pH 2.0 | pH 2.5 | pH 3.0 | pH 3.5 | pH 4.0 | pH 4.5 | pH 5.0 | pH 5.5 | pH 6.0 | pH 7.0 |
|---|---|---|---|---|---|---|---|---|---|---|
| Initial | 0.135 | 0.072 | 0.044 | 0.039 | 0.041 | 0.012 | 0.039 | 0.038 | 0.044 | 0.053 |
| 40° C./75% R.H., 3 months | 13.25 | 4.40 | 0.84 | 0.36 | 0.18 | 0.14 | 0.14 | 0.24 | 0.47 | 1.42 |

Organoleptic Properties

Eslicarbazepine acetate is a bitter tasting drug. To increase the patient acceptability of the ready to use suspension, the bitterness of the API needs to be masked by using a suitable combination of sweeteners and flavors. Organoleptic properties of the suspensions were evaluated for texture, taste, after taste, odor, flavor and acceptability. The suspension of Example 13 comprises bubble gum flavor, peppermint flavor, fantasy fruit masking flavor, strawberry flavor, and thaumatin and was perceived to have a good overall acceptability on the basis of tested organoleptic properties.

The compositions disclosed herein can comprise, consist essentially of, or consist of, the recited or listed active ingredient and excipients.

What is claimed:

1. An immediate release oral, ready to use suspension consisting of:
   a) eslicarbazepine acetate present at about 10% w/w;
   b) a mixture of microcrystalline cellulose and sodium carboxymethyl cellulose present at about 1.25% w/w;
   c) polysorbate 80 present at from about 0.01% to about 7% w/w;
   d) at least one paraben preservative present at from about 0.001% to about 4% w/w;
   e) citric acid and trisodium citrate buffer present at from about 0.01% to about 15% w/w of the composition to adjust the pH to a range of pH 3 to pH 6;
   f) sorbitol or thaumatin or a combination thereof present at from about 0.01% w/w to about 70% w/w of the composition;
   g) at least one flavoring agent present at from about 0.01% to about 5% w/w of the composition;
   h) glycerin and
   i) water, wherein the glycerin and water in combination are present at from about 10% to about 95% w/w;
   wherein the suspension is free of xanthan gum and polyoxyethylene stearate.

2. The immediate release oral pharmaceutical ready to use suspension of claim 1, wherein there is no change in the polymorphic form of eslicarbazepine for at least 5 days when the suspension is stored at 80° C.

3. The immediate release oral pharmaceutical ready to use suspension of claim 1, wherein the suspension is stable when stored at 40° C./75% R.H. for a period of at least 1 month.

4. The immediate release oral pharmaceutical ready to use suspension of claim 1, wherein the viscosity of the suspension is from 321 cps to 370 cps when stored for up to one month at 40° C./75% R.H. as measured by a Brookfield viscometer using spindle LV-3 at 50 rpm and 25° C.

5. The immediate release oral ready to use suspension of claim 1, wherein the eslicarbazepine acetate has a $D_{90}$ particle size between 5 µm and 50 µm.

6. The immediate release oral pharmaceutical ready to use suspension of claim 1, wherein the suspension exhibits more than 75% of drug release within 15 minutes, when placed in a dissolution vessel filled with 1000 ml of acetate buffer, pH 4.5 maintained at 37±0.5° C. and stirred at a paddle speed of 100 rpm using a USP Type II (paddle) apparatus.

7. The immediate release oral ready to use suspension of claim 1, wherein the suspension is bioequivalent to marketed eslicarbazepine acetate Oral Tablets 200 mg, 400 mg, 600 mg and 800 mg.

8. A kit comprising:
(a) the immediate release oral pharmaceutical ready to use suspension of claim 1; and
(b) a dispensing and/or dosing syringe or a measuring cup for administering the suspension.

9. The immediate release oral, ready to use suspension of claim 1 consisting of:
(a) Eslicarbazepine acetate present at about 10% w/w;
(b) the mixture of microcrystalline cellulose and sodium carboxymethyl cellulose present at about 1.25% w/w;
(c) the polysorbate 80 present at about 0.04% w/w;
(d) the citric acid and trisodium citrate buffer present at about 0.25 w/w;
(e) the at least one paraben preservative present at from about 0.001% to about 4% w/w;
(f) the sorbitol and thaumatin present at about 10.2% w/w;
(g) the at least one flavoring agent present at about 0.32% w/w; and
(h) the glycerin and water present at from about 20% to about 95% w/w;
wherein the pH of the suspension is from 3 to 6.5 and the suspension is free of xanthan gum and polyoxyethylene stearate.

10. The immediate release oral ready to use suspension of claim 1, wherein the sedimentation ratio is 1 after six days storage.

11. A pharmaceutically acceptable suspension of eslicarbazepine acetate consisting of:
eslicarbazepine acetate present at about 5 to 10% w/w;
a combination microcrystalline cellulose and sodium carboxymethylcellulose present at about 1.25 to 2.5% w/w;
sorbitol present at about 10-20% w/w; polysorbate 80;
thaumatin;
one or more parabens;
one or more pH adjusting agents present in an amount to adjust the pH in the range of pH 3 to pH 6.5;
one or more flavoring agents;
glycerin; and
water.

12. The pharmaceutically acceptable suspension of eslicarbazepine acetate of claim 11, wherein the suspension consists of:
eslicarbazepine acetate present at about 5 to 10% w/w;
the combination of microcrystalline cellulose and sodium carboxymethylcellulose present at about 1.25 to 2.5% w/w; the polysorbate 80 present at from about 0.01% to about 7% w/w
the sorbitol present at about 10-20% w/w;
the thaumatin present at about 0.09-0.2% w/w;
the one or more parabens present at about 0.25-0.4% w/w;
the one or more pH adjusting agents consisting of citric acid and trisodium citrate present at about 0.10-0.25% w/w to adjust the pH in the range of pH 3 to pH 6.5;
the one or more flavoring agents present at about 0.08-0.32% w/w;
the glycerin present at about 10-20% w/w; and
water.

13. The immediate release oral pharmaceutical ready to use suspension of claim 11, wherein there is no change in the polymorphic form of eslicarbazepine for at least 5 days when the suspension is stored at 80° C.

14. The immediate release oral pharmaceutical ready to use suspension of claim 11, wherein the suspension is stable when stored at 40° C./75% R.H. for a period of at least 1 month.

15. The immediate release oral pharmaceutical ready to use suspension of claim 11, wherein the viscosity of the suspension is from 321 cps to 370 cps when stored for up to one month at 40° C./75% R.H. as measured by a Brookfield viscometer using spindle LV-3 at 50 rpm and 25° C.

16. The immediate release oral ready to use suspension of claim 11, wherein the eslicarbazepine acetate has a $D_{90}$ particle size between 5 µm and 50 µm.

17. The immediate release oral pharmaceutical ready to use suspension of claim 11, wherein the suspension exhibits more than 75% of drug release within 15 minutes, when placed in a dissolution vessel filled with 1000 ml of acetate buffer, pH 4.5 maintained at 37±0.5° C. and stirred at a paddle speed of 100 rpm using a USP Type II (paddle) apparatus.

18. The immediate release oral ready to use suspension of claim 11, wherein the suspension is bioequivalent to marketed eslicarbazepine acetate oral tablets 200 mg, 400 mg, 600 mg and 800 mg.

19. The immediate release oral ready to use suspension of claim 11, wherein the sedimentation ratio is 1 after six days storage.

20. A kit comprising:
(a) the immediate release oral pharmaceutical ready to use suspension of claim 11; and
(b) a dispensing and/or dosing syringe or a measuring cup for administering the suspension.

* * * * *